United States Patent [19]
Guilfoyle et al.

[11] Patent Number: 5,994,068
[45] Date of Patent: Nov. 30, 1999

[54] NUCLEIC ACID INDEXING

[75] Inventors: Richard A. Guilfoyle, Madison, Wis.; Zhen Guo, Bellevue, Wash.

[73] Assignee: Wisconsin Alumni Research Foundation, Madison, Wis.

[21] Appl. No.: 08/815,448
[22] Filed: Mar. 11, 1997
[51] Int. Cl.$^6$ .................................................. C12Q 1/68
[52] U.S. Cl. ........................... 435/6; 435/91.1; 435/91.2; 536/25.4; 935/77; 935/78
[58] Field of Search ................................. 4345/6, 5, 91.1, 4345/91.2; 536/24.3, 24.2, 25.4; 935/77.78

[56] References Cited

U.S. PATENT DOCUMENTS

| | | | |
|---|---|---|---|
| 4,725,537 | 2/1988 | Fritsch et al. | 435/6 |
| 4,752,566 | 6/1988 | Collins et al. | 435/6 |
| 4,766,062 | 8/1988 | Diamond et al. | 435/6 |
| 4,766,065 | 8/1988 | Williams et al. | 435/6 |
| 5,270,185 | 12/1993 | Margolskee | 435/91.41 |
| 5,314,801 | 5/1994 | Nycz et al. | 435/6 |
| 5,348,853 | 9/1994 | Wang et al. | 435/6 |
| 5,352,580 | 10/1994 | Spears et al. | 435/6 |
| 5,389,515 | 2/1995 | Chmelo et al. | 435/6 |
| 5,445,933 | 8/1995 | Eadie et al. | 435/6 |
| 5,508,169 | 4/1996 | Deugau | 435/6 |
| 5,512,458 | 4/1996 | Leonard | 435/91.1 |
| 5,552,278 | 9/1996 | Brenner | 435/6 |
| 5,599,675 | 2/1997 | Brenner | 435/6 |
| 5,700,644 | 12/1997 | Gould et al. | 435/6 |
| 5,707,807 | 1/1998 | Kato | 435/6 |
| 5,710,000 | 1/1998 | Sapolsky et al. | 435/6 |
| 5,728,524 | 3/1998 | Sibson | 435/6 |
| 5,824,481 | 10/1998 | Kambara et al. | 435/6 |

FOREIGN PATENT DOCUMENTS

| | | |
|---|---|---|
| 0 224 126 A2 | 11/1985 | European Pat. Off. . |
| 0 450 370 A1 | 3/1991 | European Pat. Off. . |

OTHER PUBLICATIONS

Liang, PEng, et al., "Analysis of Altered Gene Expression by Differential Display," *Methods in Enzymology*, 254:304–321 (1995)/.

Lisitsyn, Mikolai, et al., "Representational Difference Analysis in detection of Genetic Lesions in Cancer," *Methods in Enzymology*, 254:291–303 (1995).

Lisitsyn, Mikolai, et al, "Cloning the Differences Between Two Complex Genomes," *Science*, 259:946–951 (Feb. 12, 1993).

Perucho, Manuel, et al., "Fingerprinting of DNA and RNA by Arbitrarily Primed Polymerase Chain reaction: Applications in Cancer Research," *Methods in Enzymology*, 254:275–290 (1995).

Rosenberg, Michael, "RFLP subtraction": A method for making libraries of polymorphic markers, *Process Natl. Acad. Sci. USA*, 92:6113–6117 (Jun. 1994).

Smith, Douglas R., "Ligation–medicated PCR of Restriction Fragments from LArge DNA Molecules," *PCR Methods and Applications*, 2:231–27 (1992).

Kalisch, Bernd W., et al., Covalently linked sequencing primer linkers (splinkers) for sequence analysis of restriction fragments (Recombinant DNA; hairpin ligation; synthetic oligodeoxynucleotides; dideoxynucleotides), *Gene* 44:263–270 (1986).

Unrau, Paul, et al., "Non–Cloning amplification of specific DNA fragments from whole genomic DNA digests using DNA 'indexers'," *Gene*, 145:163–169 (1994).

(List continued on next page.)

*Primary Examiner*—Ardin H. Marschel
*Attorney, Agent, or Firm*—Quarles & Brady LLP

[57] ABSTRACT

A restriction site indexing method for selectively amplifying any fragment generated by a Class II restriction enzyme includes adaptors specific to fragment ends containing adaptor indexing sequences complementary to fragment indexing sequences near the termini of fragments generated by Class II enzyme cleavage. A method for combinatorial indexing facilitates amplification of restriction fragments whose sequence is not known.

46 Claims, 4 Drawing Sheets

OTHER PUBLICATIONS

Vos, Pieter, et al., "AFLP: a new technique for DNA fingerprinting," *Nucleic Acids Research*, 23(21):4407–4414 (1995).

Zheleznaya, L.A., et al., A Method for Selective PCR–Amplification of Genomic DNA Fragments (SAGF Method), *Biochemistry (Moscow)*, 60:1037–1043.

Guilfoyle, Richard A., et al., "Ligation–mediated PCR amplification of specific fragments from a Class–II restriction endonuclease total digest," *Nucleic Acids Research*, 25(9): 1854–1858 (1997).

Quartin, Robin S., et al., "Branch Migration Mediated DNA Labeling and Cloning," *Biochemistry*, 28:8676–8682 (1989).

Weinstock, Peter H., et al., "Branch capture reactions: effect of recipient structure," *Nucleic Acids Research*, 18(14):42074213 (1990).

Wong, Daphne M., et al., "Branch capture reactions: displacers derived from asymmetric PCR," *Nucleic Acids Research*, 19(9):22512259 (1991).

Guo, et al., Abstract entitled "Feasibility of Performing 'Restriction Hybridization Ordering' (RHO) on Glass Supports," Genome Sequencing and Analysis Conference VII, Hilton Head, SC (1995).

Hayden, et al., Abstract entitled "'Restriction Hybridization Ordering' (RHO): A Front–End Assembly Strategy for Low–Pass, High–Coverage Sequencing of Shotgun Cloned DNA," Genome Sequencing and Analysis Conference VII, Hilton Head, SC (1995).

New England Biolabs Catalog pp. 92–95, 1993.

Boehringer Mannheim Catalog pp. 80–83, 1993.

Stratagene Catalog pp. 140–142, 1993.

Prashar et al. Proc. Natl. Acad. Sci., USA 93:659–663, Jan. 1996.

A. *END-SPECIFIC ADAPTORS*

<u>LEFT</u> *w/forward primer*

| -21M13 | 5' | tgtaaaacgacggccagt |
|---|---|---|
| 517L | 3' | ACATTTGCTGCCGGTCA<u>CTAGT</u>GGTC |
| 560L | | ACATTTGCTGCCGGTCA<u>CTAGT</u>GGTA |
| 1567L | | ACATTTGCTGCCGGTCA<u>CTAGT</u>GATA |
| 2684L | | ACATTTGCTGCCGGTCA<u>CTAGT</u>AGTC |
| 4459L | | ACATTTGCTGCCGGTCA<u>CTAGT</u>GGGC |
| 4623L | | ACATTTGCTGCCGGTCA<u>CTAGT</u>CAAG |
| 6330L | | ACATTTGCTGCCGGTCA<u>CTAGT</u>CAAA |
| 18909L | | ACATTTGCTGCCGGTCA<u>CTAGT</u>CGGC |

<u>RIGHT</u> *w/reverse primer*

| M13RevP | 5' | caggaaacagctatgacc |
|---|---|---|
| 517R | 3' | GTCCTTTGTCGATACTGG<u>CTAGT</u>GAAG |
| 1576R | | GTCCTTTGTCGATACTGG<u>CTAGT</u>CAGT |
| 2684R | | GTCCTTTGTCGATACTGG<u>CTAGT</u>CGGA |
| 4459R | | GTCCTTTGTCGATACTGG<u>CTAGT</u>GGAG |
| 4623R | | GTCCTTTGTCGATACTGG<u>CTAGT</u>TCCT |
| 6330R | | GTCCTTTGTCGATACTGG<u>CTAGT</u>TGAC |
| 8848R | | GTCCTTTGTCGATACTGG<u>CTAGT</u>TTAG |
| 18909R | | GTCCTTTGTCGATACTGG<u>CTAGT</u>GGTG |

B. *COMBINATORIAL ADAPTORS w/forward or reverse primer*

| Combo-FP | 5' | tgtaaaacgacggccagt |
|---|---|---|
| | 3' | ACATTTGCTGCCGGTCA<u>CTAGT</u>NNNN |
| Combo-RP | 5' | caggaaacagctatgacc |
| | 3' | GTCCTTTGTCGATACTGG<u>CTAGT</u>NNNN |

FIG 3

DpnII adaptors w/forward primer

```
5'      tgtaaaacgacggccagt
3'      ACATTTTGCTGCCGGTCACTAGGACC
        ACATTTTGCTGCCGGTCACTAGCGAC
        ACATTTTGCTGCCGGTCACTAGCCGA
        ACATTTTGCTGCCGGTCACTAGGAGA
```

NlaIII adaptor w/reverse primer

```
5'      CAGGAAACAGCTATGACCCATG
3'      GTCCTTTGTCGATACTGG
```

FIG 4

NUCLEIC ACID INDEXING

This invention was made with United States government support awarded by the following agencies: DOE, Grant No. DE-FG02-91ER61122, Case No. S-89,006; and NIH, Grant No. HG00321. The United States government has certain rights in this invention.

BACKGROUND OF THE INVENTION

It is known in the art of molecular biology that a nucleic acid fragment lying between two identified and unique primer sequences can be amplified using the polymerase chain reaction (PCR) or modifications of the PCR. PCR avoids conventional molecular cloning techniques that require the existence in nucleic acid of advantageous restriction endonuclease cleavage sites. One identified shortcoming of PCR is that fragments greater than about 40 kilobase pairs between the PCR primers are only weakly amplified. It has been difficult to obtain meaningful sequence data from large genomic fragments, particularly when such fragments are resistant to traditional cloning methods. Thus, the art is seeking new methods to obtain the nucleic acid sequences of long, uncharacterized regions of genetic material.

Efforts to amplify a specific DNA cleavage fragment from a population of such fragments have included methods that involve cleaving the DNA using Class IIS enzymes or interrupted palindrome enzymes to form fragments having non-specific terminal 5' or 3' overhangs of various lengths (generally 2 to 5 bases). Smith, D. R., *PCR Methods and Applications* 2:21–27, Cold Spring Harbor Laboratory Press (1992); Unrau, P. and K. Deugau, *Gene* 145:163–169 (1994); U.S. Pat. No. 5,508,169 (Deugau et al.); Zheleznaya, L. A. et al., *Biochemistry* (Moscow) 60:1037–1043 (1995). Class IIS enzymes cleave DNA asymmetrically at precise distances from their recognition sequences. Interrupted palindrome ("IP") enzymes cleave symmetrically between a pair of interrupted palindromic binding sites. To amplify the products of such cleavages, nucleic acid indexing linkers, containing protruding single strands complementary to the cohesive ends of Class IIS- or IP cleavage sites (rather than recognition sequences) and PCR primer sites, have been annealed and ligated to fragments generated by Class IIS- or IP cleavage.

The overhangs vary in base composition, and are determined by the locations of the enzymes, cleavage sites in a genome. The base composition and sequence of the overhang created after cleavage with a Class IIS or IP enzyme cannot be predicted because the sites at which those enzymes cleave DNA are determined by spatial relationship to the recognition sequence, but are not sequence-determined. In the methods described by Smith, Unrau, Deugau and Zheleznaya, the unique cleavage sites generated by Class IIS and IP enzymes determined a random sequence by which fragments could be indexed. However, that is not the case with more popular Class II enzymes that cleave within their recognition sites and generate predictable, identical sticky ends on each restriction fragment. Also, Unrau's method employs temperatures that result in a problem of illegitimate base pairing as well as problems with primer dimers, where indexing fragments anneal with one another rather with the target DNA.

What is desired is an indexing system that relies upon fragments not generated by Class IIS or IP enzymes, and which offer improved amplification specificity.

BRIEF SUMMARY OF THE INVENTION

The present invention is summarized in that oligonucleotide adaptors for directing PCR amplification can be engineered to efficiently and selectively hybridize "fragment indexing sequences" of one or more bases immediately adjacent to a Class II restriction enzyme recognition sites at the termini of a nucleic acid fragment. A Class II enzyme cleaves nucleic acid within its recognition site to generate a characteristic 5' or 3' overhanging end or blunt end. The recognition site can include one or more bases that do not form part of the end that results from enzymatic cleavage. When the adaptor and the nucleic acid fragment are brought together under conditions suitable for inter-strand hybridization, the invading strand of the adaptor displaces a portion of the nucleic acid fragment.

Each oligonucleotide adaptor comprises a duplex portion and a single-stranded portion. The duplex portion comprises an invading strand and a complementary PCR primer strand hybridized to the invading (displacing) strand. The oligonucleotide adaptors for the two termini are distinct, in that the PCR primer strands (and their complements on the invading strand) of each end adaptor are selected to specifically amplify fragments in the forward or reverse direction. In the case of adapters that mate with 5' overhanging termini, the PCR primer strand, which contains the sequence that is the same as that used for a PCR primer, provides a 3'- OH group that is required to join the adaptor to the restriction fragment in the method. The invading strand, which is longer than the PCR primer strand, also includes a protruding single-stranded portion that comprises (1) a nucleic acid sequence that can hybridize to the characteristic overhang and (2) an adaptor indexing sequence that is perfectly complementary to the fragment indexing sequence. The adaptor indexing sequence is provided at the 5' end of the single-stranded portion of the invading strand. In the case of adapters that mate with 3' overhanging termini, the primer-complementary strand provides a 5' phosphate for ligation to the 3' overhanging end of the restriction fragment.

The invention is further summarized in that oligonucleotide adaptors of the type described can be used in a method for amplifying a restriction fragment that includes the steps of:

(a) cleaving linear or circular nucleic acid at a restriction enzyme recognition site with at least one rare-cutting Class II restriction enzyme to generate a linear restriction fragment having a characteristic 5' or 3' overhang at each fragment terminus;

(b) hybridizing to each terminus of the fragment an end-specific oligonucleotide adaptor, thereby displacing one strand of the fragment;

(c) enzymatically ligating the restriction fragment to the primer strand to form a strand-displaced structure; and (d) amplifying the strand-displaced structure.

The invention is further summarized in that a combinatorial degenerate mixture of oligonucleotide adaptors comprising every indexing sequence is also useful in a method for combinatorial indexing.

In a related aspect, the invention is summarized in that in a method for combinatorial indexing, genetic material cleaved with a rare-cutting enzyme produces a set of fragments for subsequent amplification. The cleaved DNA is added into an array of separate amplification reactions, where each reaction contains both an adaptor specific for one fragment indexing sequence and the degenerate combinatorial mixture of all indexing adaptors specific to the other end of the fragment. Undesired complexity in reaction processing is avoided by including both the single end-specific adaptor and the combinatorial array of adaptors in the hybridization step.

In addition to obtaining valuable sequence data from the amplified fragments, it is possible to order the fragments by generating a restriction map by performing cross-digestion using two or more different enzyme arrays. By selecting the adaptor sequence, various PCR-related methods can be employed directly on the amplification products, including PCR sequencing.

It is an object of the present invention to facilitate accessing and sequencing regions of the human genome that are resistant to molecular cloning.

It is another object of the present invention to amplify nucleic acid fragments with specificity.

It is a feature of the present invention that the overhang generated by cleavage with a Class II enzyme is predictable and invariant for each enzyme.

It is another feature of the present invention that the indexing sequence is separate from (not a part of) the overhang generated by restriction enzyme cleavage.

It is yet another feature of the present invention that a degenerate collection of adaptors containing all possible indexing sequences is used in combination with a defined adaptor duplex to amplify unknown sequences of enzyme-cleaved nucleic acid.

It is an advantage of the present invention that the methods rely upon Class II enzymes rather than the less common Class IIS and IP enzymes.

It is another advantage of the present invention that the hybridizing regions of the fragments and adaptors are longer than have been used in previous indexing systems.

Another advantage of the present method is the remarkable specificity with which adaptors anneal to restriction fragments when there is perfect matching between the bases of the indexing sequence and the complementary basis of the restriction fragment.

A fully automated PCR adaptor array strategy could bypass conventional cloning by simultaneously generating a restriction map and DNA fragments for subcloning or direct sequencing from 0.5 Mb in about one day while avoiding problems associated with so-called unclonable regions. If large DNA pieces are to be mapped and sequenced, the DNA (up to about 0.5 Mb) must be purified using an existing technology such as site-specific excision (RARE, achilles heel, PNA) or RARE-cutter restriction endonucleases (e.g., NotI or meganucleases (intron-encoded endonucleases)).

It is also possible to combine the method with conventional PCR, or to use the method in a process for chromosome walking from the ends of fragments using indexers determined while preparing a restriction map.

Another application for the method is in genetic mapping to amplify fragments generated in restriction fragment length polymorphism (RFLP) analysis. Amplified fragments created from such fragments would be sequence-ready and could be used directly as probes in genetic mapping. It may also be advantageous to first perform representational difference analysis (RDA) (Lisitsyn, N. et al. *Science* 259:946–951 (1993)) or RFLP-subtraction (Rosenberg, M. et al., *PNAS USA* 91:6113–6117 (1994)) to reduce the complexity.

The method could also be used as an alternative to AFLP (Vos, P. et al., *N. A. R.* 21:4407–4414 (1995)) or arbitrarily-primed-PCR for analyzing altered gene expression by differential display (Perucho, M. et al., *Methods in Enzymology* 254:275 (1995); Liang, *Methods in Enzymology* 254:304 (1995). This method would have advantages over AP-PCR such as reduced noise and cleaner probes for gene hunting, better detection of rare messages, and a requirement for a smaller number of oligonucleotides.

Other objects, advantages, and features of the present invention will become apparent upon consideration of the following detailed description taken in conjunction with the drawings.

BRIEF DESCRIPTION OF THE SEVERAL VIEWS OF THE DRAWINGS

FIG. 3A depicts the end-specific adaptors used in the preferred embodiment to amplify the internal BclI fragments of λ DNA.

FIG. 3B shows the degenerate set of combinatorial adaptors used in the preferred embodiment to provide a proof of concept of the invention.

FIG. 4 shows the end-specific adaptors used in a method for differential display of cDNAs in accordance with the present invention.

DETAILED DESCRIPTION OF THE INVENTION

Figure 1:
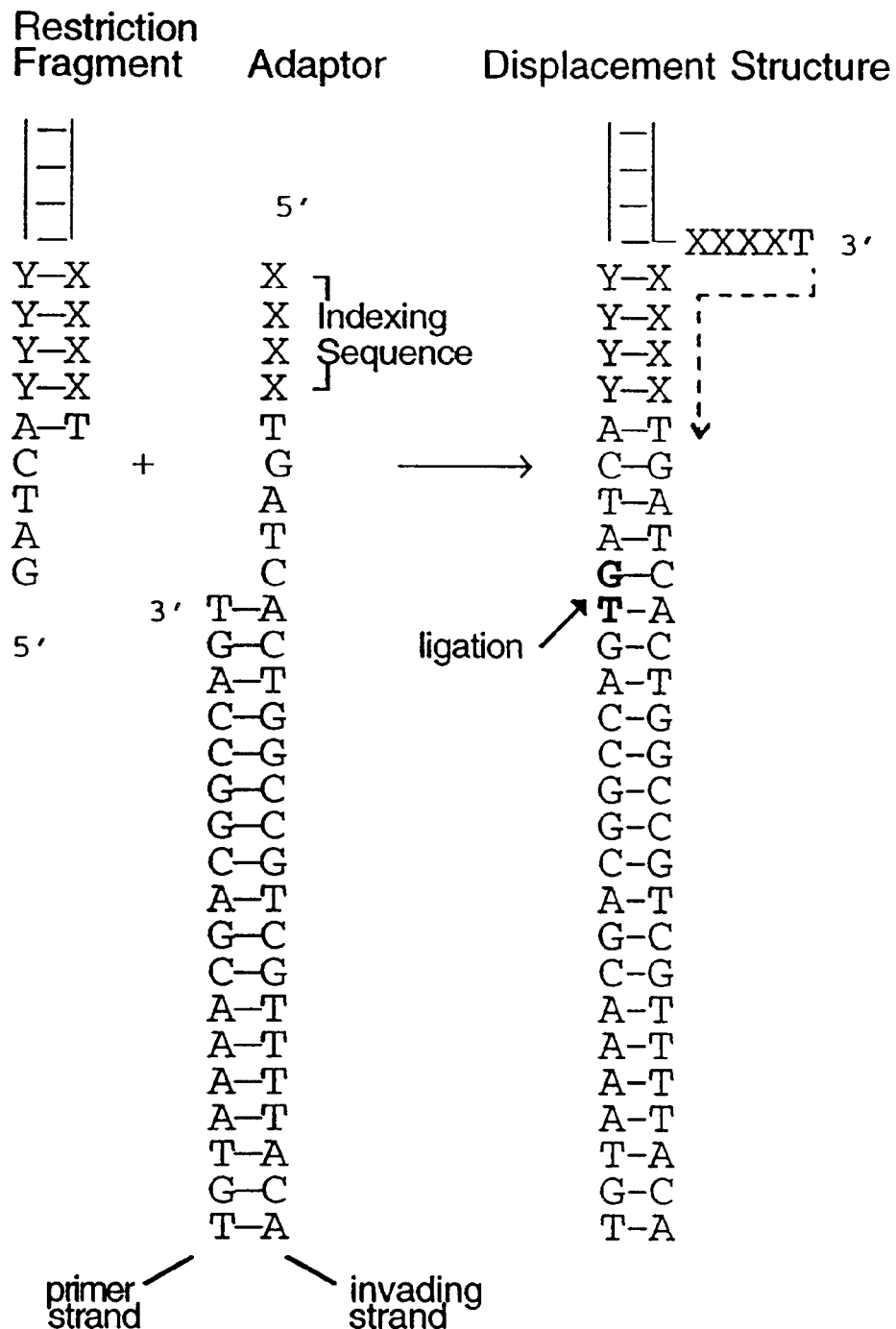
FIG. 1 shows an embodiment of the restriction site indexing method of the present invention. The figure depicts one end of a restriction fragment generated by cleavage with a Class II enzyme that generates a defined 5' overhang, a partially single stranded adaptor duplex and the displacement structure formed by hybridization and ligation of the fragment and the adaptor.
Figure 2:
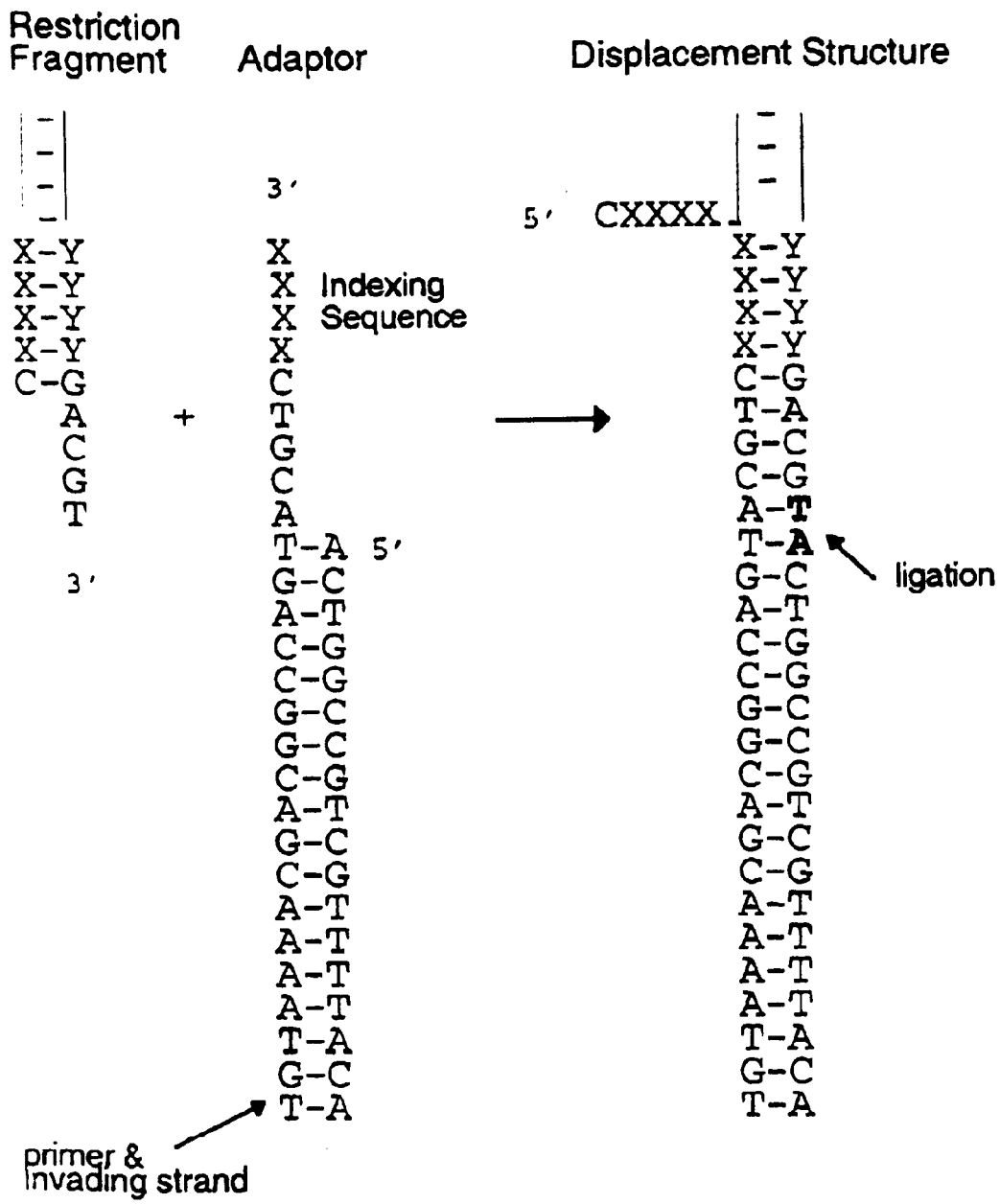
FIG. 2 shows a schematic embodiment of the invention where the restriction fragment generates a defined 3' overhang.

Reference is made to FIG. 1 which illustrates an embodiment of the restriction site indexing method of the present invention. In FIG. 1, a restriction fragment generated by cleavage with a Class II enzyme generates a defined 5' overhang (see left side of FIG. 1). In FIG. 2 (SEQ ID NO:27 through SEQ ID NO:31), a restriction fragment generated by cleavage with a Class II enzyme generates a defined 3' overhang (see left side of FIG. 2). When the enzyme generates a 3' overhang, the longer strand can act as both invading strand and primer strand. For example, in FIG. 2, the M13 forward primer (TGTAAAACGACGGCCAGT) (see also, SEQ ID NO:1) is the first 18 bases of the longer strand. The 18-mer primer oligonucleotide needs to be added for PCR amplification. No fill-in of the adaptor is required, as it is in the 5'-overhang case. Except as noted herein, the invention functions in the same manner when the enzyme generates a 3' overhang.

In the convention of this patent application, "forward" primers are specific for the "left" end of a fragment; "reverse" primers are specific for the "right" end of a fragment, where the fragment is presented with the 5'→3' strand as the top strand. As noted, a unique primer can be provided for all adaptors, if 2-strand sequencing is not desired.

Each fragment generated by cleavage of nucleic acid with a Class II restriction enzyme can be defined by a pair of fragment indexing sequences, defined as the one or more bases adjacent to the terminal recognition sites of a Class II restriction enzyme used to generate the fragment. Accordingly, a unique pair of indexing adaptors, having the partially-singled stranded structures described herein, can hybridize to the two termini of a fragment.

Even though the characteristic overhangs at the termini are identical, the fragment indexing sequences adjacent to the recognition site are not predictable; any combination of bases can reside at the indexing positions. It is noted that, because of an enzyme's cleavage strategy, one or more base pairs of the complete recognition site (e.g., in the exemplified embodiment of FIG. 1, an A-T pair) can remain near the fragment terminus and should be accommodated during adaptor design.

Adjacent to the enzyme recognition site are the bases of the fragment indexing sequence, shown in FIG. 1 as X, which can be, but need not be, identical bases. In the fragment, Y represents the base complementary to X at a given position. Thus, if X is A, Y can be T; if X is G, Y can be C; if X is C, Y can be G, and if X is T, Y can be A. Other recognized non-natural base pairs can also form. Because the fragment indexing sequence is not a part of the recognition or cleavage sequence per se, neither the indexing sequence, nor its length, are limited by the choice of enzyme. This is an advantage over ligation-mediated indexing systems known in the art.

The chance that any one indexing sequence will correspond to more than one terminus decreases as the indexing sequence length increases. Accordingly, it is desirable to select a preferred indexing sequence length. The suitable size of the fragment indexing sequence will depend upon the application to which the method is put. If the goal is specific fragment amplification, greater specificity is desired so the indexing sequence should preferably be 3, 4, or 5 bases long. However, fragment fingerprinting or differential display of cDNAs can be accomplished using a preferable indexing sequence length of 1, 2, or 3 bases. An upper limit of 10 bases in the indexing sequence is contemplated.

By way of example only, the case of preparing adaptors for amplifying a fragment is considered. There are 64 3-base-long indexing sequences, 256 4-base-long indexing sequences, and 1024 5-base-long indexing sequences. A 4-base-long indexing sequence (256 choices) is preferred. Three- or five-base-long indexing sequences could possibly be used, although if a shorter sequence were used, the selectivity would be compromised (in the sense that more fragments would be amplified per adaptor pair), and if a longer sequence were employed, sample handling becomes increasingly difficult because of the array size.

It is also desirable to select a preferred nucleic acid cleavage frequency. If many fragments are generated, the likelihood that more than one fragment will be recognized by identical adaptor pairs increases. One of ordinary skill will appreciate that the desired number of fragments will depend upon the application to which the method is put. If few fragments are generated, PCR amplification of longer fragments (with the accompanying art-recognized difficulties) will be required.

Thus a rare-cutting enzyme is preferred. In methods for restriction mapping or DNA fingerprinting, and for complex genomes, the preferred restriction enzyme used to cleave the target DNA is a 6-cutter. Five-cutters could be used, except that they are few in number and recognize degenerate sequences, thereby adding to the complexity of the required adaptors. Four-cutters are thought to be unsuitable because of their abundant distribution of cleavage sites. Enzymes cutting at sites of greater than 6 bases are also believed to be unfeasible, given their extreme rarity in the genome. On the other hand, for genomes of lower complexity, or for RNA fingerprinting (using cDNA targets) and differential display applications, 4-cutter enzymes would be suitable. Combinations of enzymes having different cleavage frequencies can be well suited for generating fragments having a certain desired average size, or for a particular target sequence.

A simple calculation for 6-cutters predicts that 256 individual, sequence-ready restriction fragments can be amplified from a target DNA of up to 0.5 megabases (Mb) in size. DNA of 1 Mb complexity digested with a 6-cutter enzyme, which cleaves a random sequence on average every 4096 base pairs, will produce 244 fragments, on average. Dividing this by 256 indexers yields about 1 amplified fragment per end-specific adaptor/combinatorial adaptor pair used. An indexing sequence would be present twice in the full library (array) of adaptors, with one contributed by the end-specific adaptor and the second by the combinatorial adaptor. A fragment would be amplified twice, but at different locations in the array, and therefore a 0.5 Mb target DNA segment would be accommodated bidirectionally for isolating individually amplified restriction fragments. If the target DNA is greater than 0.5 Mb, the method is still applicable using either complete digests or partial random digests such that more than one restriction fragment may be amplified per well.

The above-noted combination furnishes the convenience of easy to automate arrays of 256 members and a distribution of restriction sites that yields amplification lengths compatible with state-of-the-art PCR amplification technology.

The center of FIG. 1 shows an indexing adaptor of the type described. Indexing adaptors contain a region for PCR priming (or other function), a region complementary to a Class II restriction enzyme recognition site, and a strand-displacement region which is complementary to the fragment indexing sequence adjacent to the recognition site on the overhang strand.

Although it is referred to herein for convenience as the PCR primer strand, the strand can comprise any sequence that is desired to be placed at a terminus of a fragment having the specified indexing sequence and can provide any desired function, for example, a restriction enzyme recognition/cleavage site, to facilitate subsequent processing of amplified fragments. Thus, the adaptors of the present invention have appreciably broader utility than for PCR amplification. If the function to be provided by the adaptor is PCR amplification, then the sequence should be unique or present in low copy number, should provide an available 3' end that can be recognized by a suitable polymerase enzyme, such as Taq or TthI polymerase when the sequence is hybridized to a template strand. The −21M13 forward primer or the M13revP reverse primer (together, "the M13 primers") are suitable primers if the amplified fragments will be used for subsequent bi-directional sequencing. The −21M13 and M13revP primers are specific for the left and right ends of a restriction fragment, as those terms are used herein. The M13 primers, used as described herein, permit amplified fragments to be sequenced on both strands. If bi-directional sequencing is not desired, distinct primers need not be provided. For terminal fragments of linear nucleic acid molecules, a suitable amplicon-specific terminal primer can be provided in place of an adaptor if the terminal sequence is known.

The invading strand includes a portion complementary to the primer strand. Also, adjacent to that portion is a sequence that can hybridize to the Class II enzyme recognition site of the fragment terminus (including any residual bases near the fragment terminus that do not form part of the overhang) to form the displacement structure shown at the right in FIG. 1. Note that although a second displacement structure, wherein the indexing sequence is displaced by the restriction fragment, could form, it is not favored and is not observed, for it results in a net loss of 5 nucleotides available for annealing by the invading strand.

DNA ligase efficiently joins the adaptor to the restriction fragment only if the adaptor indexing sequence is perfectly complementary to the corresponding fragment indexing sequence. Even one mismatched base in the adaptor indexing sequence will discourage efficient ligation and subsequent PCR amplification relative to a perfectly matched adaptor.

However, the hybridizing portion need not be completely complementary to the overhang, in the sense of classic Watson-Crick base pairing. A universal mismatch base analog (such as the abasic 3-nitropyrrole) could be positioned within the restriction site to elicit an effect on the indexing sequence moiety. Moreover, a string of such base analogs could be used to completely replace every base within the restriction site, so that all four indexer bases could experience enhanced discrimination and a universal adaptor could be developed for most 6-cutter restriction enzymes. This would require that the base analog or analogs incorporated not greatly affect ligase activity.

By positioning an abasic universal mismatch in 3 to 4 base proximity to a natural base mismatch, the $T_m$ is lowered by up to 8° C. relative to a perfect match. This discrimination enables one to amplify only fragments that perfectly match the indexing sequence provided from a digest containing many fragments. Although this can lower overall duplex stability by as much as 15° C., the enhanced discrimination would be significant for the indexing sequences. This is because discrimination is generally reduced at natural base mismatches near 3' ends, for example, where the indexer sequences are located in the adaptor oligonucleotides.

Both positional and compositional differences may have an effect upon hybridization efficiency. It is anticipated that differences in discrimination by adaptors for indexing sequences may relate to GC content, illegitimate base pairing issues, proximity to the site of ligase joining, and contiguous base stacking effects.

One or more natural base analogs (such as 5-nitroindole) can also be added to the overhanging 5' end of an adaptor, if desired, to center the indexing sequence in the hybridizing portion thereby further enhance discrimination between exact and mismatched indexing sequences. The number of such bases that can be added can be as long as the number of bases in the portion of the invading strand that is complementary to the restriction recognition sequence.

Improved discrimination is most apparent when the universal mismatch nucleotide is provided in either of the first two positions adjacent to the indexing sequence unless the position is itself adjacent to a mismatch, which causes reduced stability. When the universal mismatch is provided any closer than three bases from the site at which subsequent ligation occurs, it is thought that the non-natural base interferes with ligation efficiency and less amplified product is produced relative to that amount produced after combining the adaptor having a perfectly matched indexing sequence.

The indexing adaptor can be formed by hybridizing a primer strand and an invading strand together under standard annealing conditions. A primer strand and an invading strand can be synthesized separately using oligonucleotide synthesis methods that are conventional in the art. Many oligonucleotide primers for use as primer strands are readily commercially available. The M13 primers are commercially available, are in widespread use, and can be fluorescently tagged. In addition, the M13 primers have annealing temperatures that are very close to one another. This property is desirable in that both the forward and reverse amplifications can proceed with comparable efficiency under a single set of conditions. As noted, the two sequencing primers need not be used if direct sequencing is not desired.

The invention can be embodied in a method for amplifying fragments of known sequence, using readily engineered adaptors having suitable adaptor indexing sequences specific for both ends of the known fragment. Also, by providing combinatorial mixtures comprising all possible adaptors specific to the fragment ends, one can amplify any fragment without knowing the identity of the indexing sequence specific for either terminus. The invention can also be practiced on a fragment where one end is known but the other end is unknown, by employing in the method one end-specific adaptor or amplicon-specific primer for the known fragment end and a combinatorial adaptor mixture for the other fragment end thereby permitting amplification of a fragment containing known and unknown sequences, such as intron regions and flanking sequences beyond viral junctions.

The method is applicable to various targets including previously "unclonable" regions from genomic DNA, since there is no need to clone such fragments to obtain useful DNA sequence. Also, large fragments can be directly cleaved and isolated from complex genomes for subsequent analysis using the method. Also, intron sequences, the sequences flanking viral integrants, can be isolated and sequenced, as can terminal fragments from YAC, BAC, P1, plasmid or cosmid clones. The method can also be used to generate STS-like probes at rare-cutter restriction sites. Also, it will be possible to excise fragments surrounding regions of ambiguous sequence for further sequencing using the method.

In a method embodying the present invention, a population of fragments is generated from a nucleic acid sample by cleaving the sample with a Class II restriction enzyme. The identity of the Class II restriction enzyme is not critical, except to the extent that the sequence of the terminal overhang must be known, for preparing suitable adaptors. When selecting a restriction enzyme and designing the respective adaptors for use with that enzyme for restriction mapping or isolation of "sequence-ready" fragments, it is advantageous, but not essential, to minimize the differences in the composition of the recognition site by forming an overhang whose 4 bases are G, A, T and C. Any of about 50 known Class II 6-cutters (including isoschizomers) generate 3' or 5' overhangs whose 4 bases are G, A, T and C. The available enzymes include, but are not limited to, BamHI, HindIII, AvrII, ApaLI, KpnI, SphI, NsiI, and SacI. Among these enzymes, only the outermost base remaining after cleavage will vary in composition. The outermost base makes only a small and almost inconsequential contribution to the $T_m$ for adaptor-fragment annealing. This facilitates the ligation protocol, but is not to be considered essential to the invention. This design parameter also facilitates the method by helping to confine discrimination analysis to the base composition of the indexer sequences. In addition to Class II enzymes that generate four base overhangs, other enzymes that may be used effectively in the method are those that cleave palindromic sequences in opposite polarity, those that leave either blunt ends or different length overhangs (e.g., not 4-base overhangs), and those that leave base compositions other than A, G, T, and C.

After cleavage, one or more pairs of partially single-stranded indexing adaptors are hybridized under standard annealing conditions to the termini of one or more fragments generated by the enzyme cleavage. Each fragment can hybridize to a single pair of adaptors. As noted above, the sequence that complements the restriction recognition sequence can include an universal mismatch to improve discrimination between adaptor indexing sequences that are perfectly-matched and imperfectly-matched to the fragment indexing sequences. Bona fide amplification occurs when adaptors containing perfectly-matched indexing sequences are hybridized, thus there is advantage to favoring the ability of such sequences to hybridize. Hybridization should be sufficiently strong to permit subsequent ligation of fragment termini to a pair of adaptors.

After hybridization, the gap between the primer strand and the overhanging strand of the restriction fragment is closed by treating the structure with DNA ligase under standard conditions (see FIG. 1, right side), thereby joining the overhanging strand to the primer strand. T4 ligase (NEB), thermostable Ampligase (Epicenter Technologies) ligase enzymes are suitable and have been used successfully at temperatures up to 50° C. Other ligases may also be used. Suitable ligation conditions are typical of those used in the art. The result of this step is to introduce an end-specific PCR primer (or other desired sequence) onto each end of each fragment. The primer is attached only to fragments bearing a suitable indexing sequence.

Note that during hybridization the single-stranded portion of the adaptor hybridizes to its complementary sequence on the overhang strand and displaces the fragment indexing sequence (and any residual bases of the recognition site) on the opposite strand. In the special case of a 5' terminal overhanging fragment (shown in FIG. 1), the invading strand is not covalently joined to the restriction fragment. Thus, before amplification can proceed, the displaced strand is extended from its 3'-end by polymerase in the first thermal cycle to regenerate a template complementary to the PCR primer. This extension step is not required if the termini have 3' overhangs (FIG. 2).

Fragments can be amplified using standard PCR reactions such as those described in the Example. In the preferred embodiment, one set of PCR conditions is suitable to amplify fragments of most sizes, although it may be necessary in certain cases to adjust the PCR conditions in accordance with the abilities of one skilled in the art to amplify a particular fragment. PCR protocols can be varied to accommodate particular sequences and primers. One skilled in the art will appreciate that certain modifications to the PCR protocols may be required to amplify particular fragments. Such modifications may include varying primer length, adjusting magnesium concentration, adjusting thermal cycle time, adjusting the annealing temperature and the like. It is necessary to add additional primer before amplifying. One skilled in the art will also appreciate, for example, that so-called long distance PCR conditions can be employed to amplify fragments greater than about 3 kb, although success under such conditions cannot be assured, as such protocols are still under development by the art.

Occasional false amplifications may be observed if a particular indexing sequence forms a more stable mismatch when hybridizing with the restriction fragment. However, one having ordinary skill can determine hybridization conditions under which such mismatches are not observed and do not give rise to amplification products.

In another aspect, the invention is also a system for combinatorial indexing. Combinatorial indexing is advantageously employed when seeking to separately amplify restriction fragments where the index sequence of each fragment terminus is not known. It will be appreciated that by providing every adaptor specific to both ends, all fragments generated by enzyme cleavage can be amplified, even without a priori knowledge of the sequence. In the method described above, by contrast, each fragment terminus has an indexing sequence selected from one of the possible indexing sequences (e.g., 1 of 256 possible 4-base-long indexing sequences). The unique combination of indexing sequences corresponding to the termini of an unknown fragment is one of 65,536 possible pairwise combinations of 256 left-end-specific indexing sequences and 256 right-end-specific indexing sequences.

Such a large array of possible combinations is methodologically impractical (even if automated), but would be necessary to recover all possible restriction fragments that could be generated from total digestion of a larger DNA. Even if automated, the handling of such a large array would be formidable. However, the size of the array can be reduced to 256 simply by providing in each reaction a single unique left or right end-specific adaptor along with a degenerate mixture of 256 adaptors corresponding to the second fragment end. Such mixtures are referred to herein as a "combinatorial adaptor" or a "C-adaptor." The C-adaptor mixture can be made in a single oligodeoxynucleotide synthesis process by providing all 4 nucleotides (A, G, C, T) at each adaptor indexing sequence position.

A PCR reaction would yield an amplified fragment only when it contains both the end-specific indexing sequence as well as to one of the indexing sequences in the combinatorial adaptor. In 256 separate ligation/PCR reactions, the probability is that each reaction amplifies a single, sequence-ready restriction fragment. Although the invention is practiced by providing an adaptor specific to each end when 2-strand direct sequencing of the PCR products is desired, the invention can also be practiced by providing a single primer for both ends. The invention can also be practiced using a single adaptor, if PCR amplification is not desired. For example, a restriction fragment and a primer strand tagged with a reporter molecule can be annealed to a surface-bound invading strand, without subsequent ligation. The restriction fragment will anneal to the invading strand where there is correspondence between the adaptor- and fragment indexing sequences. The primer strand will also anneal to the invading strand. After annealing, unbound restriction fragments can be washed away. Interstrand base stacking interactions between the tagged primer strand and the restriction fragment will keep the primer strand annealed only where the fragment corresponds to the invading strand indexing sequence. This can facilitate specific detection of restriction fragments of interest. When used in this manner, the invention provides a method for ordering fragments in a clone.

To map the order of fragments, several independent arrays are analyzed as described using adaptors specific for different restriction enzymes and then the product of each array can be cross-digested with the enzymes of the other digestions. The products of those cross-digestions can be separated by electrophoresis and a standard restriction map can be produced for any nucleic acid fragment.

Ligation-mediated indexing using class-II enzymes can be applied to RNA fingerprinting in a way similar to that described for class-IIS enzymes (Kato, K. NAR, 24:394–395 (1996), incorporated herein by reference). A particular application in this regard would be for functional identification of genes by differential cDNA display. Kato and others proposed that an indexing approach could offer several advantages over the more commonly used "arbitrarily primed PCR" (Liang, P. and Pardee, A. B. Science, 257:967–971 (1992), incorporated herein by reference) for this purpose, including (a) obtaining more coding regions, (b) allowing lower redundancy, and (c) detecting rare messages more efficiently.

An important aspect of such a fingerprinting application is the ability to adequately resolve the fragments generated. For example, differentiated or neoplastic somatic cells have a messenger RNA complexity on the order of $20 \times 10^6$. Using a pair of 4-cutter restriction enzymes to digest cDNA, fragments are obtained that should, on average, be <200 bp in size. A given message will be represented by numerous non-overlapping fragments specifically amplified using adaptors with 4-nucleotide indexing sequences. The fingerprint of the 256 fragment subclasses generated can be well resolved on a polyacrylamide gel.

The order of the fragments for a given message can be determined either by (a) restriction mapping and/or sequencing the clone(s) from an appropriate cDNA library that cross-hybridize to the amplified fragments, or (b) amplifying the cDNA using the identified message-specific indexing adaptors in conjunction with primers which can access the 5'- and/or 3'-end of the message, and then restriction mapping and/or sequencing. As examples, the 5'-end of an mRNA can be located after preparing the cDNA using CapFinder technology (Clontech); the 3'-end of an mRNA can be accessed using oligo-dT primers as described by Liang and Pardee or oligo-dT coupled with a different or universal primer.

Single-enzyme strategies could also be used to obtain RNA fingerprints using indexers for class-II enzymes. Indexing can be confined to one of the cleaving enzymes if the second cleaving enzyme generates a constant, defined end. These strategies would target either the 5'-proximal or 3'-proximal restriction fragments of the cDNA. The cDNA could be cut with a single 4-cutter, ligated to the indexing adaptors containing a universal primer, and then PCR amplified by using either a CapFinder or oligo-dT associated primer. These approaches would yield less complex fingerprints than the double-enzyme approach, but would be biased toward detecting fewer coding regions and more untranslated regions (UTRs). However, UTRs represent excellent signatures for identifying unique messages.

Different strategies could be adopted to reduce array size and, therefore, sample handling. One strategy could utilize the combinatorial adaptors. Instead of using 256 single-end adaptors, adaptors could be pooled in several combinatorial mixtures which represent subclasses of the complete library (e.g. 4 pools×64; 16 pools×16, etc.). (A pooled subclass could also be synthesized as a degenerate oligo). The complexity of the banding pattern (per pool) will decrease as the number of pools increases. In another strategy, 3-nucleotide indexing sequences could be utilized. The size of a 3-nucleotide indexing sequence library would be 64. However, because trinucleotide frequencies are higher than tetranucleotide frequencies in a given genome, a more complex banding pattern is expected.

EXAMPLE

The feasibility of the method described herein was tested using $N^6$-methyladenine-free bacteriophage λ DNA (48502 base pairs, New England Biolabs, Beverly, Mass.) as the model amplicon system and BclI, a 6-cutter, as the model Class II restriction endonuclease. Enzyme digestions were performed in the supplier's buffer at 37° C. for two hours with 20 U of BclI in a volume of 100 µl. BclI cuts the λ genome eight times, producing nine fragments that share the same 5'-overhang sequence, 5'-GATC. BclI was chosen because of the broad range of fragment sizes that the enzyme generates: 517, 560, 1576, 2684, 4459, 4623, 6330, 8844, and 18909 base pairs. The terminal fragments are 560 and 8844 base pairs. The terminal fragments include a BclI cut site at one end and the genome terminus at the other. Unique oligonucleotide primers were used to amplify the terminal λ fragments.

Since the entire nucleic acid sequence of the λ genome is known, adaptors were produced containing only the required adaptor indexing sequences. In the adaptors, the primer strand was either an M13 sequencing primer or M13 reverse sequencing primer, depending upon which end of the fragment it was specific for. Terminal primers were provided for the terminal fragments. The invading strand comprised, in 5' to 3' order, a 4-base-long indexing sequence, a 5-base-long sequence complementary to the BclI recognition site, and a portion fully and perfectly complementary to the primer strand. The primer strand and the invading strand were prepared by conventional oligonucleotide synthesis, were purified on Sep-Pak C18 cartridges and were annealed at a concentration of 12.8 µM of each primer in 50 mM tris-HCl, pH 7.8 at 85° C. The oligonucleotides were allowed to anneal by slow cooling to room temperature.

The end-specific indexing sequences used to amplify particular λ BclI fragments are shown in FIG. 3A (SEQ ID NO:1 through SEQ ID NO:20). The end-specific adaptors that corresponded to the left (L) and right (R) ends of the fragments used the −21M13 (forward) and M13RevP (reverse) universal primer sequences, respectively. For each end, the primer strand is shown once and each partially-complementary end-specific invading strand is shown. The indexing sequences specific to each fragment end are shown in bold and the BclI site that remains after cleavage is underlined.

Once the adaptors were prepared, the BclI fragments were individually amplified from the total BclI digest as follows:

(a) 5 µg of $N^6$-methyladenine-free λ DNA (New England Biolabs, Beverly, Mass.) was digested at 37° C. or 2 hours with 20 units of BclI in a volume of 100 µl using the manufacturer's (NEB) buffer;

(b) 15 ng of digested λ DNA were combined with left and right adaptor pairs corresponding to a particular restriction fragment in NEB 1 X ligase buffer for 5 minutes at 40° C. (each ligation contained 25 pmols of single end adaptor pairs, in equal amounts. For the right end of the genome, λ-specific primer CGTAACCTGTCGGATCAC (SEQ ID NO:21) was used. To amplify the left end of the genome (8848L), λ-specific oligonucleotide CGCGGGTTTTCGC-TATTT (SEQ ID NO:22) was used);

(c) 800 units of NEB T4 DNA ligase were added and the reactions were incubated for 20 minutes at 40° C. and were stopped by heating to 65° C. for 15 minutes;

(d) 1.5 ng of λ DNA were transferred to 100 µl PCR reactions. All PCR reactions were performed with the XL-PCR kit (Perkin-Elmer, Applied Biosystems Division, Foster City, Calif.), using 2 µl (4 units) of rTth DNA polymerase. The PCR reactions included 1.1 mM magnesium acetate (1 mM $MgCl_2$ carried over from the ligase reaction), except the amplification of the 4,459 base pair BclI fragment from λ DNA which included 1.65 µl of magnesium acetate to obtain robust and specific amplification from its combinatorial adaptor. The specific products could also be obtained using 0.55 mM magnesium acetate. All PCR reactions contained 10 pmols of appropriate primer oligonucleotides. PCR was performed in the PTC-200 DNA engine (MJ Research, Watertown, Mass.) using the following thermal cycling profile: 95° C. for 1.5 minutes followed by 30 cycles of 94° C. for 40 seconds, 55° C. for 40 seconds, 72° C. for 5 minutes. Treatment with 3'-to-5' exonuclease activity of Vent polymerase was important for increasing the yields of the PCR products obtained with rTth polymerase.

(e) 20 µl were loaded on 0.8% agarose gels containing 0.5 µg per µl ethidium bromide. Specific bands were observed upon electrophoresis.

No reactant removal or product purifications were required between steps, making the overall procedure amenable to automation. In some conditions, it may be advantageous, but not absolutely necessary, to purify fragment-bound adaptors away from unligated adaptors or fragments. A solid-phase purification step can be included. However, the need for such a solid-phase purification has not been observed.

When the appropriate left/right adaptor pairs or terminal/left or right adaptor pairs were used, eight of the nine BclI fragments of λ DNA were selectively and specifically amplified. Specific amplification of the 18909 base pair fragment was not observed, although the fragment was observed with additional non-specific fragments. It is believed that the fragment can be specifically amplified by more specifically defining reaction conditions or thermal cycling parameters.

It is possible to achieve good discrimination among the adaptor pairs tested. Where non-targeted restriction fragments were co-amplified along with the desired product, the extra amplification can be explained by homology in some indexing sequence positions and the potential for stable mis-match duplex formation in other indexing sequence positions. Few non-specific products that did not co-migrate with the restriction fragments were observed.

To demonstrate the utility of the method employing combinatorial adaptors, two sets of combinatorial primers were prepared, as is shown in FIG. 3B. The "combo-FP" adaptor included the −21M13 primer hybridized to the indicated C-adaptors, where N at each position indicated in the adaptor represents a population of all four nucleotides at that position. Thus, each mixture of combinatorial adaptors included 256 different adaptors. Likewise, the "combo-RP" adaptor set included the M13revP primer hybridized to the indicated set of invading strands where N is all four nucleotides at each position.

To amplify various fragments of BclI-cut λ DNA, the following amounts of the indicated end-specific adaptors (or primers in the case of the terminal fragments) were combined with the indicated amounts of combo-FP or combo-RP mixtures.

TABLE I

| Fragment to be amplified (bp) | Right adaptors (pmol) | Left adaptors (pmol) | Combo-FP mix (pmol) | Combo-RP mix (pmol) |
|---|---|---|---|---|
| 517 | — | — | — | — |
| 560 | 10 (560R*) | — | 0.0025 | — |
| 1576 | 25 | — | 0.5 | — |
| 2684 | 25 | — | 0.25 | — |
| 4459 | 25 | — | 25 | — |
| 4623 | 25 pmol | — | 25 | — |
| 6330 | — | — | — | — |
| 8848 | — | 10 (8848L*) | — | 0.0025 |

*Primer only (in PCR reaction)

Specific amplification of fragments having the expected fragment length were observed by polyacrylamide gel electrophoresis, thus indicating that desired fragments can be amplified by providing an adaptor specific for one end of a desired fragment and a mixture of adaptors containing an adaptor specific for the indexing sequence at the other end of the fragment. It is of note that no purification was required prior to PCR amplification to remove ligation reactants or intermediate products.

Specific fragment amplification was driven predominantly by the end-specific adaptor ligated at one end. That is because when the end-specific adaptor and C-adaptors are provided at equimolar amounts, the relative concentration of a single indexing sequence in the combinatorial mixture is only 1/256 as great as the amount of the end-specific adaptor, thereby favoring more efficient ligation of the more prevalent adaptor.

In additional tests, it was shown that specific fragments were amplified from the total BclI-λ DNA digest over a range of asymmetric end-specific:C-adaptor concentration ratios. The ratios of end-specific adaptors:C-adaptors was varied from 1:1 to 100:1. An additional hundred-fold dilution of the combinatorial adaptor yielded the most specific λ terminal fragment amplifications.

To demonstrate that specific amplification can be accomplished in the presence of a more complex genome, E. coli DNA containing λc1857Sam7dam⁻ lysogen (NEB) was used as the amplification target. This more complex genome (4.7 Mb) has 1,604 BclI sites, 200 times as may as λ DNA. Despite this increase in target complexity, λ BclI fragments could still be specifically amplified using the adaptors tested.

Eighteen µg of the λ lysogen DNA was digested with BclI. Twenty five pmol (each) of left and right adaptors were used to amplify the 517, 1576, and 2684 bp fragments. Subsequent dilutions and reactions were performed as described above for λ DNA.

Although the concept has been demonstrated using known DNA, it is equally applicable to unknown DNA targets excised directly from the genome. Using the method, a DNA fragment that maps between two STS markers can be obtained. At least two 6-cutter arrays will be used in conjunction with combinatorial indexing to obtain a complete restriction map of the selected fragment and the production of contigs. PCR amplification products produced from each array will be subjected to agarose gel electrophoresis to acquire fragment length information.

RNA fingerprinting using adaptors for class-II enzymes was tested for the differential display of cDNA from rat mammary carcinomas, untreated or treated with perillyl alcohol (PA) which is a monoterpene used for chemoprevention and chemotherapy (Crowell, P. L. and Gould, M. N. Crit. Rev. Oncog., 5L:1-22 (1994), incorporated herein by reference). cDNA from treated and untreated tumors (at half-regression) was prepared by and according to Ariazi, E. and Gould, M. (J. Biol. Chem., 271:29286–29294 (1996), incorporated herein by reference).

In a preliminary study, DpnII (GATC) and NlaIII (CATG) were used as the cleavage enzymes. DpnII provides indexing sequences next to its 5'-overhang and NlaIII provides a defined 3'-overhang for a cohesive end adaptor. Because a DpnII site will not anneal with an NlaIII site, fragment chimeras are minimized and primer-dimer formation during PCR is eliminated. As is shown in FIG. 4, the NlaIII adaptor contains the M13 reverse primer sequence and the DpnII adaptors contain the M13 forward primer sequence. For this study, four 4-nucleotide indexing sequences were used (FIG. 4, SEQ ID NO:1 and SEQ ID NO:23 through SEQ ID NO:28). The adaptors were designed such that the chance of forming stable mismatches was minimized according to the observations of Ebel et al., *Biochemistry* 31:12083–12086 (1992), incorporated herein by reference.

A suitable protocol for generating fingerprints was as follows. Note that if the enzyme cleavage buffers are compatible with one another, the cleavages can be accomplished in a double digestion.

(1) digest 0.5 μg cDNA (−/+ PA treatment) with NlaIII;
(2) clean-up*, elute in water;
(3) join NlaIII adaptor (25 pmol) with 800 U T4 DNA ligase at 37° C.;
(4) clean-up, elute in water;
(5) digest with Dpn II;
(6) clean-up, elute in water;
(7) split cDNA four ways (125 ng ea.) and join Dpn II adaptors (25 pmol) with 800 U T4 DNA ligase at 40° C.;
(8) use Klentaq (Advantage cDNA PCR kit, Clontech, Palo Alto, Calif.) to amplify 5 ng of ligated DNA using 25 pmol ea. of the −21M13 and M13rev primers;
(9) run aliquots on 5% polyacrylamide electrophoresis gels; stain with Sybr Green I (Molecular Probes, Eugene, Oreg.) to separate and visualize a characteristic pattern for amplified fragments;
(10) visualize by UV transillumination or laser scanning (Fluorimager 575, Molecular Dynamics, Sunnyvale, Calif.)

each clean-up step used Qiaquick spin column (Qiagen, Chatsworth, Calif.) to remove enzymes, buffers and/or unligated adaptors For the two 4-cutter approach, an average expected number of amplified products per gel lane (i.e. per indexer) was estimated by $(20 \times 10^6/512)/256$, or approximately 150, assuming a perfectly random distribution of sites and a perfectly random sequence of nucleotides in the total cDNA. However, because the sequences are not random in nature, fragment size range varies. For the 4 indexing adaptors tested, the size of the observed amplified fragments ranged from about 50 bp to 300 bp. The bands were well separated and indicated a quasi-random distribution of restriction sites useful for fingerprinting and probe isolations. The fingerprints observed were highly reproducible for a given set of thermal cycling parameters and yielded differentially expressed bands indicating both up-regulation and down-regulation after PA treatment (confirmed by varying the amount of template in the PCR). The sensitivity of the assay was high, detecting as little as 2–3 fold changes in the levels of some differentially expressed bands. However, to distinguish truly differentially expressed bands from false positives, it would typically be necessary to re-amplify a band and use it as a probe against Northern blots.

The present invention is not intended to be limited to the preceding embodiments, but rather to encompass all such variations and modifications as come within the scope of the appended claims.

We claim:

1. A method for indexing polynucleotides, comprising the steps of:

(A) combining under base-pairing conditions:
  (i) one or more distinguishable sets of one or more indexing adaptors, each adaptor comprising at least one single-stranded terminus having an end, the single-stranded terminus characterized by, in non-overlapping order inward from the end: (a) an indexing sequence n bases long and (b) a sequence characteristic of cleavage by a Class II restriction endonuclease, wherein n is a positive integer, and
  (ii) one or more polynucleotides corresponding to one or more adaptors in the one or more sets of adaptors, wherein a corresponding polynucleotide comprises at least one terminus having an end, the terminus characterized by, in non-overlapping order inward from the end: (a) a region having a sequence characteristic of cleavage by a Class II restriction endonuclease and (b) a double-stranded region having on one strand a sequence that base-pairs with an indexing sequence of an adaptor and on the other strand a sequence complementary thereto;

(B) base-pairing at least one adaptor terminus and at least one corresponding polynucleotide terminus to form at least one strand-displaced structure wherein the indexing sequence of the single-stranded adaptor terminus is base-paired with the sequence that base-pairs with an indexing sequence of the terminus of the corresponding polynucleotide, and the complementary sequence on the other strand of the polynucleotide terminus is displaced from base-pairing thereto;

(C) for each adaptor set, distinguishing the corresponding polynucleotides that form strand-displaced structures, thereby indexing the polynucleotides by their base-pairing to the distinguishable sets of adaptors.

2. A method according to claim 1, wherein n is 1 to 4.

3. A method according to claim 2, wherein n is 2, 3 or 4.

4. A method according to claim 1, wherein the indexing adaptors in all the sets of adaptors together comprise indexing sequences that can base pair to all the sequences said n bases long that can be formed by the bases A, C, G and T.

5. A method according to claim 1, wherein the at least one strand-displaced structure comprises a displacing strand and a non-displacing strand, the method further comprising the step of ligating, in the strand-displaced structure, the end of the non-displacing strand to the end of the abutting strand of the double-stranded region of the corresponding polynucleotide.

6. A method according to claim 1, wherein one or more adaptors further comprise a sequence for amplifying the corresponding polynucleotide.

7. A method according to claim 1, wherein strand-displaced structures are formed at both termini of at least one corresponding polynucleotide.

8. A method according to claim 7, wherein the adaptor at each terminus of at least one corresponding polynucleotide further comprises at least one sequence for amplifying a corresponding polynucleotide by PCR.

9. A method according to claim 8, wherein the strand-displaced structures comprise a displacing strand and a non-displacing strand, the method further comprising the step of ligating, in the strand-displaced structure at each terminus of at least one polynucleotide, the end of the non-displacing strand to the end of the abutting strand of the double-stranded region of the corresponding polynucleotide.

10. A method according to claim 9, further comprising the step of amplifying by PCR corresponding polynucleotides having non-displacing strands ligated to each terminus, using primers defined by the sequence in the adaptor for amplifying a corresponding polynucleotide.

11. A method according to claim 6, further comprising the step of amplifying at least one polynucleotide using primers defined by the sequence in the adaptor for amplifying a corresponding polynucleotide.

12. A method according to claim 1, wherein the sequence characteristic of cleavage by a Class II restriction endonuclease has a 3'-terminated single-stranded region.

13. A method according to claim 1, wherein the sequence characteristic of cleavage by a Class II restriction endonuclease has a 5'-terminated single-stranded region.

14. A method according to claim 1, wherein the sequence characteristic of cleavage by a Class II restriction endonuclease has a blunt end.

15. A method for characterizing a population of polynucleotides, comprising the steps of;

(A) combining under base-pairing conditions:

(i) one or more distinguishable sets of one or more indexing adaptors, each adaptor comprising at least one single-stranded terminus having an end, the single-stranded terminus characterized by, in non-overlapping order inward from the end: (a) an indexing sequence n bases long and (b) a sequence characteristic of cleavage by a Class II restriction endonuclease, wherein n is a positive integer, and (ii) a population of polynucleotides that includes one or more polynucleotides corresponding to one or more adaptors in the one or more set of adaptors, wherein a corresponding polynucleotide comprises at least one terminus having an end, the terminus characterized by, in non-overlapping order inward from the end: (a) a region having a sequence characteristic of cleavage by a Class II restriction endonuclease and (b) a double-stranded region having on one strand a sequence that base-pairs with an indexing sequence of an adaptor and on the other strand a sequence complementary thereto;

(B) base-pairing at least one adaptor terminus to at least one corresponding polynucleotide terminus to form at least one strand-displaced structure wherein the indexing sequence of the single-stranded adaptor terminus is base-paired with the sequence that base-pairs with an indexing sequence of the terminus of the corresponding polynucleotide, and the complementary sequence on the other strand of the polynucleotide terminus is displaced from base-pairing thereto; and (C) for each adaptor set, characterizing the population of polynucleotides by detecting one or more corresponding polynucleotides that form strand-displaced structures, or the absence thereof.

16. A method according to claim 15, wherein n is 1 to 5.

17. A method according to claim 15, wherein the population is a population of cDNAs or other polynucleotides representative of mRNAs.

18. A method according to claim 17, wherein the characterization is indicative of gene expression in a sample from which the population was derived.

19. A method according to claim 15, wherein the population is a population of genomic DNAs or polynucleotides representative of genomic DNAs.

20. A method according to claim 19, wherein the characterization comprises characterizing mutations or the absence thereof in: (a) the sequence characteristic of cleavage by a Class II restriction endonuclease; (b) the indexing sequence or both (a) and (b) of one or more corresponding polynucleotides in the population.

21. A method according to claim 20, wherein the absence or presence of a mutation thus characterized in one or more corresponding polynucleotides is diagnostic of a potential to develop one or more diseases, or of one or more diseases.

22. A method according to claim 15, further comprising the step of ligating, in a strand-displaced structure, the end of the adaptor-strand comprising the indexing sequence to the end of the abutting strand of the double-stranded region of the corresponding polynucleotide.

23. A method according to claim 15, wherein one or more adaptors further comprise a sequence for amplifying a corresponding polynucleotide.

24. A method according to claim 15, wherein strand-displaced structures are formed at both termini of at least one corresponding polynucleotide.

25. A method according to claim 24, wherein the adaptor at each terminus of at least one corresponding polynucleotide further comprises at least one sequence for amplifying a corresponding polynucleotide by PCR.

26. A method according to claim 25, wherein the strand-displaced structures comprise a displacing strand and a non-displacing strand, the method further comprising the step of ligating, in the strand-displaced structure at each terminus of at least one polynucleotide, the end of the non-displacing strand to the end of the abutting strand of the double-stranded region of the corresponding polynucleotide.

27. A method according to claim 26, further comprising the step of amplifying by PCR corresponding polynucleotides having non-displacing strands ligated to each terminus, using primers defined by the sequence in the adaptor for amplifying a corresponding polynucleotide.

28. A method according to claim 15, further comprising, for at least one adaptor set, resolving from one another at least two corresponding polynucleotides that form strand-displaced structures.

29. A method according to claim 28, wherein the population is a population of cDNAs or other polynucleotides representative of mRNAs in a sample, the size and the quantity of the resolved corresponding polynucleotides is determined, each resolved corresponding polynucleotide is identified by the indexing sequence and the Class II restriction endonuclease characteristic sequence of the adaptor set with which it formed a strand-displaced structure and by its size, and the quantities of the thus identified corresponding polynucleotides for at least two adaptor sets provides a profile of gene expression in the source from which the cDNA was derived.

30. A method according to claim 28, wherein corresponding polynucleotides for at least one set of adaptors are resolved by size by electrophoresis.

31. A method according to claim 29, wherein the sequences characteristic of a Class II restriction endonuclease and the indexing sequences of the adaptor sets together subdivide the cDNAs or other polynucleotides representative of the mRNAs into sets of corresponding polynucleotides in each of which corresponding polynucleotides can be differentiated by electrophoresis.

32. A method for comparing mRNA in two or more samples, comprising the steps of claim 29 to generate a profile of gene expression of a first sample and a profile of gene expression in a second sample and comparing the profiles of the first and second samples.

33. A method for amplifying at least one polynucleotide, the method comprising the steps of:
    (A) combining under base-pairing conditions:
        (1) an adaptor comprising: (a) a sequence for amplifying a polynucleotide and (b) at least one single-stranded terminus having an end, the single-stranded terminus characterized by, in non-overlapping order inward from the end, (i) a sequence n bases long for base-pairing to one or more polynucleotides, where n is a positive integer and (ii) a sequence characteristic of cleavage by a Class II restriction endonuclease,
        (2) at least one polynucleotide comprising at least one terminus having an end, the terminus characterized by, in non-overlapping order inward from the end, (a) a region having a sequence characteristic of cleavage by a Class II restriction endonuclease and (b) a double-stranded region having on one strand a sequence that base-pairs with the single-stranded adaptor sequence for base-pairing with a polynucleotide, and on the other strand a sequence complementary thereto, and
        (3) a non-invading strand that base pairs to the adaptor at a region other than the single-stranded terminus, the non-invading strand having an end;
    (B) base-pairing the single-stranded adaptor sequence for base-pairing to one or more polynucleotides with the polynucleotide sequence that base-pairs therewith and displacing the complementary sequence on the other strand of the polynucleotide terminus;
    (C) ligating the end of the non-invading strand to the end of the abutting strand of the double-stranded region of the polynucleotide; and
    (D) amplifying at least one polynucleotide using primer defined by the sequence in the adaptor for amplifying a polynucleotide.

34. A method according to claim 33, wherein the sequence for amplifying a polynucleotide is complementary to a sequence of a primer for elongating a template by a DNA polymerase.

35. A method according to claim 34 wherein adaptors are ligated at both ends of the polynucleotide and exponential amplification of the polynucleotide is carried out by PCR using primers defined by the sequences of the adaptors for amplifying a polynucleotide.

36. A method according to claim 33, wherein more than two adaptors each having a different sequence for base-pairing with a polynucleotide are used to base pair specifically to different polynucleotides in a population of polynucleotides.

37. A method according to claim 33, wherein an adaptor is ligated to each end of the polynucleotides and exponential amplification of the polynucleotides is carried out by PCR using primers defined by the adaptor sequences for amplifying the polynucleotides.

38. A method according to claim 37, wherein the sequences of the adaptors for base-pairing to one or more polynucleotides together comprise indexing sequences that can base pair to all the sequences said n bases long that can be formed by the bases A, C, G and T.

39. A method according to claim 33 wherein the sequence for amplifying a polynucleotide is a sequence of a primer for elongating a template by a DNA polymerase.

40. A method for isolating a polynucleotide, comprising the steps of:
    (A) combining under base-pairing conditions:
        (1) an adaptor comprising: (a) a sequence for amplifying a polynucleotide and (b) at least one single-stranded terminus having an end, the single-stranded terminus characterized by, in non-overlapping order inward from the end, (i) a sequence n bases long for base-pairing to a polynucleotide, where n is a positive integer and (ii) a sequence characteristic of cleavage by a Class II restriction endonuclease, and
        (2) a polynucleotide comprising at least one terminus having an end, the terminus characterized by, in non-overlapping order inward from the end, (a) a region having a sequence characteristic of cleavage by a Class II restriction endonuclease and (b) a double-stranded region having on one strand a sequence that base-pairs with the single-stranded adaptor sequence for base-pairing with a polynucleotide, and on the other strand a sequence complementary thereto, and
        (3) a non-invading strand that base pairs to the adaptor at a region other than the single-stranded terminus, the non-invading strand having an end;
    (B) base-pairing the single-stranded adaptor sequence for base-pairing to a polynucleotide with the polynucleotide sequence that base-pairs therewith and displacing the complementary sequence on the other strand of the polynucleotide terminus;
    (C) ligating the end of the non-invading strand to the end of the abutting strand of the double-stranded region of the polynucleotide;

(D) amplifying the polynucleotide using the adaptor sequence for amplifying a polynucleotide; and (E) isolating the amplified polynucleotide.

41. A method according to claim 40, wherein the sequence for amplifying a polynucleotide is selected from the group consisting of a primer for elongating a template by a DNA polymerase and a sequence complementary to a primer for elongating a template by a DNA polymerase.

42. A method according to 41, wherein adaptors are ligated at both ends of the polynucleotide and exponential amplification of the polynucleotide is carried out by PCR using primers defined by the sequences of the adaptors for amplifying a polynucleotide.

43. A method according to claim 40, wherein two or more adaptors each having a different sequence for base-pairing with a polynucleotide are used to base pair specifically to two or more different polynucleotides in a population of polynucleotides.

44. A method according to claim 43, wherein an adaptor is ligated to each end of the polynucleotides and exponential amplification of the polynucleotides is carried out by PCR using primers defined by the sequences of the adaptors for amplifying a polynucleotide.

45. A method according to claim 40, wherein the step of isolating the amplified polynucleotide further comprises resolving the amplified polynucleotide from other polynucleotides by gel electrophoresis and then eluting the amplified polynucleotide from the gel.

46. A method according to claim 40, further comprising the step of cloning the amplified polynucleotide.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "-21M13 forward primer"

(xi) SEQUENCE DESCRIPTION: SEQ ID NO:1:

TGTAAAACGA CGGCCAGT                                            18

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "end specific adaptor (517L)"

(xi) SEQUENCE DESCRIPTION: SEQ ID NO:2:

ACATTTTGCT GCCGGTCACT AGTGGTC                               27

(2) INFORMATION FOR SEQ ID NO:3:

(i) SEQUENCE CHARACTERISTICS:
      (A) LENGTH: 27 base pairs

-continued

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (560L)"

(xi) SEQUENCE DESCRIPTION: SEQ ID NO:3:

ACATTTTGCT GCCGGTCACT AGTGGTA                                              27

(2) INFORMATION FOR SEQ ID NO:4:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (1567L)"

(xi) SEQUENCE DESCRIPTION: SEQ ID NO:4:

ACATTTTGCT GCCGGTCACT AGTGATA                                              27

(2) INFORMATION FOR SEQ ID NO:5:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (2684L)"

(xi) SEQUENCE DESCRIPTION: SEQ ID NO:5:

ACATTTTGCT GCCGGTCACT AGTAGTC                                              27

(2) INFORMATION FOR SEQ ID NO:6:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (4459L)"

(xi) SEQUENCE DESCRIPTION: SEQ ID NO:6:

ACATTTTGCT GCCGGTCACT AGTGGGC                                              27

(2) INFORMATION FOR SEQ ID NO:7:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (4623L)"

(xi) SEQUENCE DESCRIPTION: SEQ ID NO:7:

ACATTTTGCT GCCGGTCACT AGTCAAG                                              27

(2) INFORMATION FOR SEQ ID NO:8:

(i) SEQUENCE CHARACTERISTICS:
            (A) LENGTH: 27 base pairs
```

(B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (6330L)"

(xi) SEQUENCE DESCRIPTION: SEQ ID NO:8:

ACATTTTGCT GCCGGTCACT AGTCAAA                                           27

(2) INFORMATION FOR SEQ ID NO:9:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (18909L)"

(xi) SEQUENCE DESCRIPTION: SEQ ID NO:9:

ACATTTTGCT GCCGGTCACT AGTCGGC                                           27

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "M13RevP reverse primer"

(xi) SEQUENCE DESCRIPTION: SEQ ID NO:10:

CAGGAAACAG CTATGACC                                                     18

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (517R)"

(xi) SEQUENCE DESCRIPTION: SEQ ID NO:11:

GTCCTTTGTC GATACTGGCT AGTGAAG                                           27

(2) INFORMATION FOR SEQ ID NO:12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (1576R)"

(xi) SEQUENCE DESCRIPTION: SEQ ID NO:12:

GTCCTTTGTC GATACTGGCT AGTCAGT                                           27

(2) INFORMATION FOR SEQ ID NO:13:

(i) SEQUENCE CHARACTERISTICS:
            (A) LENGTH: 27 base pairs

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (2684R)"

(xi) SEQUENCE DESCRIPTION: SEQ ID NO:13:

GTCCTTTGTC GATACTGGCT AGTCGGA                                              27

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (4459R)"

(xi) SEQUENCE DESCRIPTION: SEQ ID NO:14:

GTCCTTTGTC GATACTGGCT AGTGGAG                                              27

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (4623R)"

(xi) SEQUENCE DESCRIPTION: SEQ ID NO:15:

GTCCTTTGTC GATACTGGCT AGTTCCT                                              27

(2) INFORMATION FOR SEQ ID NO:16:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (6330R)"

(xi) SEQUENCE DESCRIPTION: SEQ ID NO:16:

GTCCTTTGTC GATACTGGCT AGTTGAC                                              27

(2) INFORMATION FOR SEQ ID NO:17:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (8848R)"

(xi) SEQUENCE DESCRIPTION: SEQ ID NO:17:

GTCCTTTGTC GATACTGGCT AGTTTAG                                              27

(2) INFORMATION FOR SEQ ID NO:18:

(i) SEQUENCE CHARACTERISTICS:
            (A) LENGTH: 27 base pairs
```

(B) TYPE: nucleic acid
            (C) STRANDEDNESS: single
            (D) TOPOLOGY: linear (ii) MOLECULE TYPE: other nucleic acid
            (A) DESCRIPTION: /desc = "end specific adaptor (18909R)"

(xi) SEQUENCE DESCRIPTION: SEQ ID NO:18:

GTCCTTTGTC GATACTGGCT AGTGGTG                                              27

(2) INFORMATION FOR SEQ ID NO:19:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "combinatorial adaptor invading
                strand for forward primer"

(xi) SEQUENCE DESCRIPTION: SEQ ID NO:19:

ACATTTTGCT GCCGGTCACT AGTNNNN                                              27

(2) INFORMATION FOR SEQ ID NO:20:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "combinatorial adaptor invading
                strand for reverse primer"

(xi) SEQUENCE DESCRIPTION: SEQ ID NO:20:

GTCCTTTGTC GATACTGGCT AGTNNNN                                              27

(2) INFORMATION FOR SEQ ID NO:21:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "lambda terminal primer (right end)"

(xi) SEQUENCE DESCRIPTION: SEQ ID NO:21:

CGTAACCTGT CGGATCAC                                                        18

(2) INFORMATION FOR SEQ ID NO:22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "lambda primer (left end)"

(xi) SEQUENCE DESCRIPTION: SEQ ID NO:22:

CGCGGGTTTT CGCTATTT                                                        18

(2) INFORMATION FOR SEQ ID NO:23:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "end specific adaptor"

(xi) SEQUENCE DESCRIPTION: SEQ ID NO:23:

ACATTTTGCT GCCGGTCACT AGGACC                                              26

(2) INFORMATION FOR SEQ ID NO:24:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "end specific adaptor"

(xi) SEQUENCE DESCRIPTION: SEQ ID NO:24:

ACATTTTGCT GCCGGTCACT AGCGAC                                              26

(2) INFORMATION FOR SEQ ID NO:25:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "end specific adaptor"

(xi) SEQUENCE DESCRIPTION: SEQ ID NO:25:

ACATTTTGCT GCCGGTCACT AGCCGA                                              26

(2) INFORMATION FOR SEQ ID NO:26:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "end specific adaptor"

(xi) SEQUENCE DESCRIPTION: SEQ ID NO:26:

ACATTTTGCT GCCGGTCACT AGGAGA                                              26

(2) INFORMATION FOR SEQ ID NO:27:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "M13 reverse primer with NlaIII
               adaptor"

(xi) SEQUENCE DESCRIPTION: SEQ ID NO:27:

CAGGAAACAG CTATGACCCA TG                                                  22

(2) INFORMATION FOR SEQ ID NO:28:

-continued (i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "adaptor strand"

(xi) SEQUENCE DESCRIPTION: SEQ ID NO:28:

GTCCTTTGTC GATACTGG                                              18

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "invading and primer strand for
            3'-overhang adaptor"

(xi) SEQUENCE DESCRIPTION: SEQ ID NO:29:

NNNNCTGCAT GACCGGCAGC AAAATGT                                    27

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide complementary to
            M13 forward primer"

(xi) SEQUENCE DESCRIPTION: SEQ ID NO:30:

ACATTTTGCT GCCGGTCA                                              18

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide complementary to M13
            forward primer after ligation to 3'overhang restriction
            fragment end"

(xi) SEQUENCE DESCRIPTION: SEQ ID NO:31:

ACATTTTGCT GCCGGTCATG CAGNNNN                                    27